US008992580B2

(12) United States Patent
Bar et al.

(10) Patent No.: US 8,992,580 B2
(45) Date of Patent: Mar. 31, 2015

(54) ROBOT GUIDED OBLIQUE SPINAL STABILIZATION

(75) Inventors: Yossef Bar, Tirat HaCarmel (IL); Eli Zehavi, Haifa (IL); Isador Lieberman, Plano, TX (US); Moshe Shoham, Hamovil (IL)

(73) Assignee: Mazor Robotics Ltd., Caesarea (IL)

( * ) Notice: Subject to any disclaimer, the term of this patent is extended or adjusted under 35 U.S.C. 154(b) by 785 days.

(21) Appl. No.: 13/132,095

(22) PCT Filed: Dec. 1, 2009

(86) PCT No.: PCT/IL2009/001130
§ 371 (c)(1),
(2), (4) Date: Sep. 19, 2011

(87) PCT Pub. No.: WO2010/064234
PCT Pub. Date: Jun. 10, 2010

(65) Prior Publication Data
US 2011/0319941 A1    Dec. 29, 2011

Related U.S. Application Data

(60) Provisional application No. 61/193,441, filed on Dec. 1, 2008.

(51) Int. Cl.
*A61B 17/88* (2006.01)
*A61B 17/16* (2006.01)
*A61B 17/70* (2006.01)
*A61B 17/17* (2006.01)
(Continued)

(52) U.S. Cl.
CPC ......... *A61B 17/1757* (2013.01); *A61B 17/1671* (2013.01); *A61B 19/2203* (2013.01);
(Continued)

(58) Field of Classification Search
CPC ........ A61B 17/16; A61B 17/61; A61B 17/70; A61B 17/88
USPC ................. 606/86 A, 86 R, 96, 104, 246–279
See application file for complete search history.

(56) References Cited

U.S. PATENT DOCUMENTS 6,558,390 B2    5/2003  Cragg
7,194,120 B2    3/2007  Wicker et al.
(Continued)

FOREIGN PATENT DOCUMENTS

WO    2008038282 A2    4/2008
WO    2008038284 A2    4/2008

OTHER PUBLICATIONS

PCT International Search Report and Written Opinion of the ISA, mailed Jun. 8, 2010 in PCT/IL09/01130.
(Continued)

*Primary Examiner* — Christopher Beccia
(74) *Attorney, Agent, or Firm* — Daniel Feigelson; Fourth Dimension IP

(57) ABSTRACT

A robotic system for performing minimally invasive spinal stabilization, using two screws inserted in oblique trajectories from an inferior vertebra pedicle into the adjacent superior vertebra body. The procedure is less traumatic than such procedures performed using open back surgery, by virtue of the robot used to guide the surgeon along a safe trajectory, avoiding damage to nerves surrounding the vertebrae. The robot arm is advantageous since no access is provided in a minimally invasive procedure for direct viewing of the operation site, and the accuracy required for oblique entry can readily be achieved only using robotic control. This robotic system also obviates the need for a large number of fluoroscope images to check drill insertion position relative to the surrounding nerves. Disc cleaning tools with flexible wire heads are also described. The drilling trajectory is determined by comparing fluoroscope images to preoperative images showing the planned path.

21 Claims, 10 Drawing Sheets

(51) Int. Cl.
*A61B 19/00* (2006.01)
*A61B 17/00* (2006.01)
*A61B 17/02* (2006.01)
*A61B 17/34* (2006.01)
*A61B 17/56* (2006.01)

(52) U.S. Cl.
CPC .......... *A61B17/7064* (2013.01); *A61B 19/201* (2013.01); *A61B 19/26* (2013.01); *A61B 2017/00557* (2013.01); *A61B 2017/00685* (2013.01); *A61B 2017/0256* (2013.01); *A61B 2017/3407* (2013.01); *A61B 2019/507* (2013.01); *A61B 2217/005* (2013.01); *A61B 2017/564* (2013.01)
USPC .............................. 606/279; 606/246; 606/79

(56) References Cited

U.S. PATENT DOCUMENTS

| 2004/0240715 | A1* | 12/2004 | Wicker et al. | 382/128 |
| 2005/0171557 | A1* | 8/2005 | Shoham | 606/130 |
| 2007/0055291 | A1* | 3/2007 | Birkmeyer et al. | 606/130 |
| 2008/0071272 | A1 | 3/2008 | Shoham et al. | |
| 2008/0275454 | A1* | 11/2008 | Geibel | 606/96 |
| 2009/0112269 | A1 | 4/2009 | Lieberman et al. | |
| 2009/0163957 | A1 | 6/2009 | St. Clair et al. | |

OTHER PUBLICATIONS

Article entitled "Direct Pediculo-Body Fixation in Cases of Spondylolisthesis with Advanced Intervertebral Disc Degeneration", by D. Grob et al, published in European Spine Journal, vol. 5, pp. 281-285, 1996.

Article entitled "Bone-Mounted Miniature Robot for Surgical Procedures: Concept and Clinical Applications", by Moshe Shoham et al, published in IEEE Transactions on Robotics and Automation, vol. 19, No. 5, pp. 893-901, Oct. 2003.

Extended European Supplementary Search Report dated Jul. 8, 2013 in corresponding European patent application No. 09830094.0.

* cited by examiner

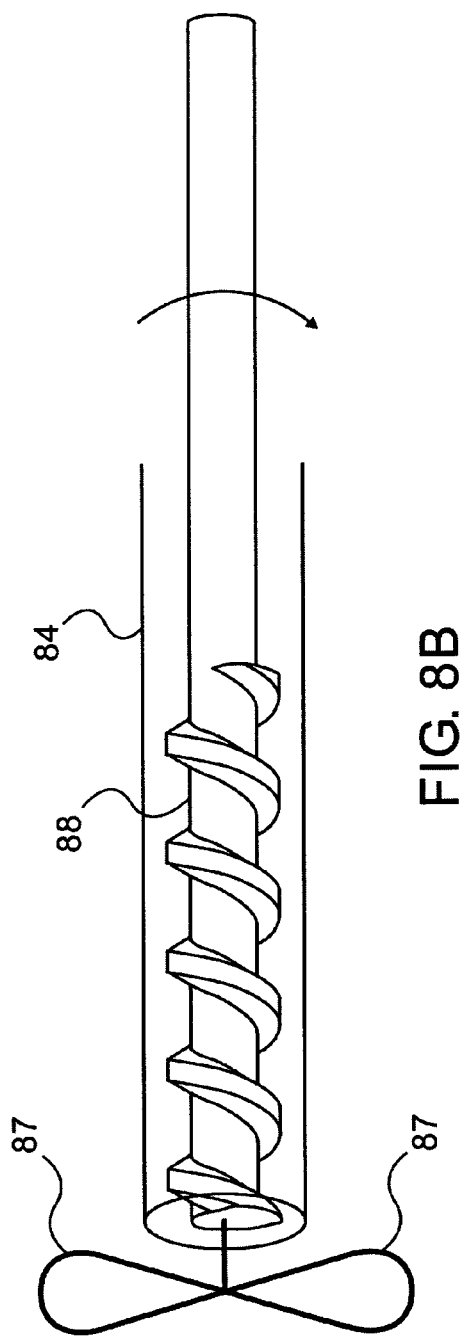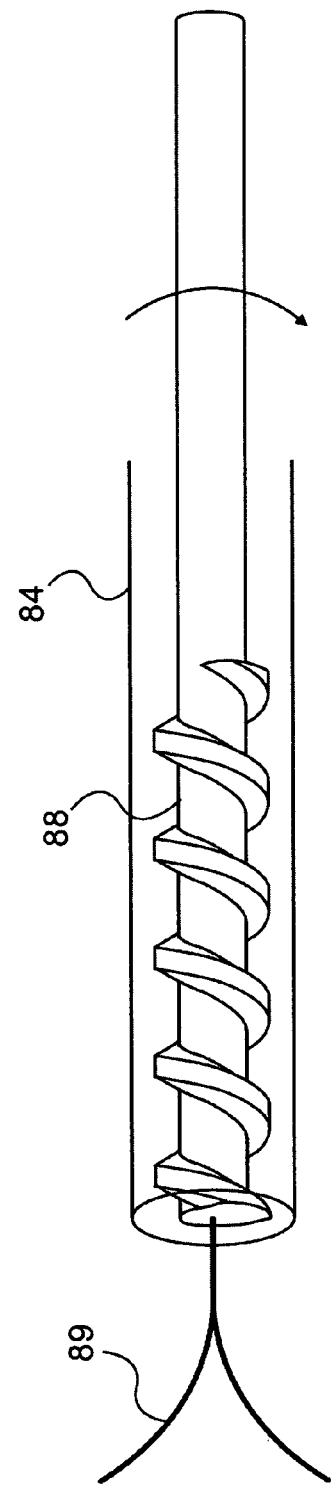

ROBOT GUIDED OBLIQUE SPINAL STABILIZATION

This is a 35 U.S.C. §371 application of PCT/IL2009/001130, filed Dec. 1, 2009, and claims the benefit under 35 U.S.C. §120 of said PCT application, and further claims the benefit under 35 U.S.C. §119(e) of U.S. Provisional Patent Application Ser. No. 61/193,441, filed Dec. 1, 2008. The contents of these priority applications are incorporated herein by reference.

FIELD OF THE INVENTION

The present invention relates to the field of vertebral stabilization techniques by means of a pair of obliquely inserted screws, especially using robotic procedures to safely generate the oblique entry paths between the inferior and superior vertebrae to be fused.

BACKGROUND OF THE INVENTION

As illustrated schematically in FIGS. 1A and 1B, a common treatment for spinal stabilization is the fixation of two or more vertebrae 10, 12, performed by insertion of a pair of screws 14, 16, into each of the vertebrae to be fused and connecting the screw heads on either side of the spine by two rigid rods 17, 18. Cleaning the disc space 15 and inserting bone graft into the cleaned disc space causes bone to grow between the vertebrae until, until several months later, the fusion is completed. FIG. 1A is a cross sectional plan view of the superior vertebra 10, while FIG. 1B is a lateral view from the left of both fused vertebrae 10, 12.

The screws are usually inserted into the pedicles 19, two for each vertebra such that a minimum of four screws are required for each level of fusion. Spinal fusion by means of pedicle screw insertion is currently the most common procedure adopted for spinal stabilization, with hundreds of thousands of cases performed each year all over the world.

A different fixation technique, using only two obliquely inserted screws, one on either side of the spine, has also been described in the article entitled "Direct Pediculo-Body Fixation in Cases of Spondylolisthesis with Advanced Intervertebral Disc Degeneration", by D. Grob et al published in European Spine Journal, Vol. 5, pp. 281-285; 1996. The surgical approach suggested in this article is for oblique transpedicular interbody fixation, and it was successfully performed at the L4-L5 and L5-S1 levels. In this technique, a pair of screws is inserted bilaterally through the pedicles of the inferior vertebra and passed diagonally across the disc space towards the anterior cortical rim of the superior vertebral body. FIG. 2A illustrates a lateral view of such a pair of vertebrae 20, 21, of a patient suffering from spondylolisthesis, showing the oblique entry of the screw 22, as described in Grob et al. Because of the anterior displacement of the upper slipped vertebra 20, the entry angle of the screw is closer to the lateral plane than 45°, the significance of which will be described hereinbelow. Grob et al also describes the use of an inward angle of 5° to 10° in the saggital direction, as will be shown in FIGS. 2B and 2C below, to ensure that the screws remain within the body of the superior vertebra 20 and do not penetrate the cortical bone thereof.

Grob et al describes the cases of 16 patients with average follow-up of 31 months (24-77 months) treated with this direct pediculo-body fixation technique. Clinical evaluation showed significant reduction in pain and increase in functionality. Radiologic evaluations indicate solid bony fusion in all cases, and no neurological or other complications were observed. The stand-alone two-screw construction was concluded to be simple to implement and clinically successful. The screws provided three-dimensional stability, which led to bony unions and favorable clinical outcomes in all patients. This procedure thus uses only two screws, rather than four screws and two rods.

Even though this procedure was performed with good success on a significant number of patients (16), the technique has not gained much acceptance in the operating room. One reason for its low acceptance may be that the required screw trajectories pass close to nerve roots, and hence a clear view of the operation site is needed to minimize the risk of damage to a nerve, whether at the spinal canal or at the foramen. This required, as described in Grob, an open surgical procedure with a large incision to expose the entire region of the oblique trajectory from the skin to the entry point at the vertebra, and towards the second vertebrae into which the screw is inserted, so that the surgeon is able to estimate accurately the correct entry position and angle. This technique was therefore highly traumatic to the tissues and muscles of the back, and this may have contributed to the lack of acceptance of the technique, despite its structural simplicity.

In this respect the procedure is different from the common spinal fusion methods using four screws per level. As illustrated in FIGS. 1A and 1B, such prior art spinal fusion methods involve a screw trajectory which remains exclusively within the vertebral bone, from the entry point at the pedicle through to the vertebral body. Unless a gross error has been made in the insertion trajectory, there is little danger of nerve damage. It is reported that only about 3% of such operations result in permanent neurological deficits with this technique. The insertion trajectory can either be determined visually by the surgeon, or can be performed robotically, based on an operative plan using pre-surgical CT images, or by use of a navigation system to define an accurate path.

In addition, because of the difficulty of safe insertion of the screws, as described in Grob, it is necessary to perform the oblique drilling under fluoroscopic control, which may involve both the patient and the operating room staff with unnecessarily significant levels of X-ray exposure.

The procedure described in Grob was performed on patients suffering from spondylolisthesis, involving significant anterior slippage of the superior vertebra and an advanced stage of disc resorption with a reduction of disc height by at least 75% of the original height. Under these conditions, and as shown in FIG. 2A, the drill enters the superior vertebra through the posterior end plate, and at an angle of less than 45° to the lateral plane, thus clearly avoiding the foramen 27. However, if the procedure were to be performed on a patient having normal vertebral alignment and a normal disc height, the entry angle would need to be tilted closer to the axial direction, thereby involving a closer encroachment to the nerve roots at the foramen. This would increase the risk of nerve damage in performing this oblique entry procedure. Furthermore, the size of the incision that has to be made in the subject's back is considerably longer for a normally aligned vertebral spine, than for a patient with spondylolisthesis, since the angle of entry of the drilling axis is closer in the case of the normally aligned spine to the axial direction of the spine. This makes the open surgery approach even less inviting as a technique for treating aligned vertebrae. Finally, it should be noted that in a significant number of patients, the vertebrae may lie several centimeters below the surface of the patient's skin, beneath layers of fat and muscle tissue, such that the additional depth from the skin to the vertebra, in combination with the angle of the trajectory to the normal, would increase the length of the incision needed even more than indicated above.

This oblique entry procedure has been described again recently, in US patent publication number US 2009/0163957 to S. St. Clair et al, for use in fusion procedures in subjects having normal vertebral separation. FIGS. 2B and 2C illustrate the position and path of entry of such a pair of obliquely inserted screws. Though the vertebral alignment in FIGS. 2B and 2C is different from that in FIG. 2A, similar items are similarly numbered to those of FIG. 2A. FIG. 2B shows schematically a posterior view of the adjacent vertebrae 20, 21, with interbody oblique fixation screws 22, showing the inward tilt of the screws as described in Grob et al., and FIG. 2C shows a lateral view of the same vertebrae. The drawings, and FIG. 2C in particular, show the path of the screws from the inferior articular process 23 of the facet joint of the inferior vertebra 21, traversing the pedicle and through the endplate 24 of the inferior vertebra, across the interbody space 28 between the vertebrae, through the inferior endplate 25 of the superior vertebra body 20, through the centrum of the superior vertebra and towards the junction 26 of the superior endplate and the anterior vertebral surface of the superior vertebra. It is observed in FIG. 2C that the entry angle in the posterior-anterior plane is at an angle of 45° or less to the longitudinal axis of the spine defined by the superior and inferior vertebrae, such that the drill trajectory passes significantly closer to the position of nerve roots at the foramen 27 than was the case with the procedures described by Grob, performed on spondylolisthesic patients. The procedures described in the US 2009/0163957 publication therefore further emphasizes the need for an apparatus and method for performing oblique stabilization or fusion more safely than the Grob prior art procedures, where only spondylolisthesic patients were treated.

The disclosures of each of the publications mentioned in this section and in other sections of the specification, are hereby incorporated by reference, each in its entirety.

SUMMARY OF THE INVENTION

The present disclosure describes new exemplary systems and methods for performing minimally invasive spinal stabilization, using only two screws inserted in oblique trajectories from an inferior vertebra pedicle into the adjacent superior vertebra body. The procedure can be less traumatic than some previously described procedures using oblique trajectories, by executing the trajectory drilling in a minimally invasive manner through two stab incisions, using a robotic arm to guide the surgeon along a safe trajectory. The robot arm is virtually essential in such a minimally invasive procedure since no access is provided for direct viewing of the operation site, and the high accuracy required for oblique entry can only be generally achieved using robotic control. This high accuracy level is mandated by the presence of nerve roots exiting the foramen in close proximity to the path required to proceed from the pedicle region of the inferior vertebra to the adjacent superior vertebra body. This robot guided system also obviates the need for a large number of fluoroscope images to check the drill insertion position relative to the nerve positions around the subject's vertebrae.

One exemplary implementation involves a system for preparing a spinal stabilization procedure between two adjacent vertebrae of a subject, the system comprising:
(i) a surgical robot mounted such that it can define at least one path for oblique screw insertion from the pedicle region in an inferior one of the two adjacent vertebrae into the body of the adjacent superior vertebra, towards its anterior cortical rim,
(ii) a control system receiving three-dimensional preoperative data, including information regarding the spatial location of the bone structures and the nerve positions of the two adjacent vertebrae, and
(iii) a registration system to relate the coordinate system of the surgical robot with the three-dimensional preoperative data,
wherein the control system is adapted to use the information to determine a safe path for the oblique screw insertion.

In such a system, the safe path may be a path in the coordinate system of the surgical robot, which does not intersect the course of a nerve of the subject, as determined from the three-dimensional preoperative data. This three-dimensional preoperative data may be obtained from CT scans, MRI scans or ultrasound images.

Additionally, the safe path may be chosen using criteria obtained from the three-dimensional preoperative data to ensure that the path does not approach any nerve roots. The above mentioned the control system should be adapted to inhibit the robot from executing a path in the coordinate system of the surgical robot, which would coincide with the course of a nerve of the subject, as determined in the three-dimensional preoperative data. Furthermore, this safe path may be determined by the control system using criteria which ensure that the path does not approach any nerve roots, nor that it can make any undesired collisions with a bone structure. Yet other implementations may involve a system such as described above, in which the safe path passes through a pedicle of the inferior vertebra, and is determined by the control system using criteria which further ensure that the safe path does not break out of the cortical wall of the pedicle.

The safe path in the coordinate system of the surgical robot may be viewed by fluoroscopic imaging or ultrasonic imaging. It should be such that the spinal stabilization procedure can be performed by minimally invasive techniques, or without direct viewing of the anatomical land marks of the inferior vertebra.

With regard to the path, it can be defined by the robot by means of a tool guide held in the robot's operating arm, such that a surgeon can drill the safe path through the tool guide. Alternatively, the system can further comprise a robotic held drill, such that the robot itself can drill the safe path.

Additionally, in further implementations of any of the above-described systems, the registration system may comprise an image processing module for comparison of anatomical topological features of the subject in the three-dimensional preoperative data with those same features in fluoroscope images of the vertebrae. Additionally, the registration system may further include a target having predefined marker features, disposed in a predetermined position and orientation relative to the robot, such that images of the target in the fluoroscope images enable the co-ordinate system of the robot to be related to that of fluoroscope images of the vertebrae. Finally, as an alternative, the registration system could utilize a navigational system to relate the coordinate system of the robot to fluoroscope images of the vertebrae.

Still other example implementations involve a method for performing spinal stabilization between two adjacent vertebrae of a subject, the method comprising:
(i) generating three-dimensional preoperative data including information regarding the spatial location of the bone structures and nerve positions associated with the two adjacent vertebrae, (ii) using the three-dimensional preoperative data to plan at least one path for oblique screw insertion, from the pedicle region in an inferior one of the two adjacent vertebrae into the body of the adjacent superior vertebra towards its anterior cortical rim, the at least one planned path avoiding nerve positions of the subject as determined in the preoperative data, (iii) mounting a surgical robot such that it can define the at least one planned path, (iv) registering the coordinate system of the robot to the three-dimensional preoperative data, (v) utilizing the surgical robot to generate a drilled hole along one of the at least one planned paths, and (vi) inserting a screw obliquely between the inferior and superior vertebrae through the drilled hole.

In such a method, the at least one planned path may be two planned paths, one on each lateral side of the vertebrae, such that two screws may be inserted obliquely between the inferior and superior vertebrae. The method may be performed minimally invasively using a percutaneous technique. In any such methods, the at least one path should also be planned to avoid any undesired collisions with a bone structure.

Furthermore, according to another exemplary implementation, the robot may define the at least one planned path by means of a tool guide held in its operating arm, and the generating of the drilled hole may then be performed by a surgeon using the tool guide.

In any of these methods, the step of registering the coordinate system of the robot to the three-dimensional preoperative data may advantageously comprise the step of comparing anatomical topological features of the subject in the three-dimensional preoperative data with those same features in fluoroscope images of the vertebrae. Such a registration method may further comprise the step of disposing a target having known markers, in a predetermined position and orientation relative to the robot, such that images thereof in the fluoroscope images enable the co-ordinate system of the robot to be related to that of fluoroscope images of the vertebrae. Alternatively, the step of relating the co-ordinate system of the robot to fluoroscope images of the vertebrae may be achieved by means of a navigational system.

Another exemplary implementation involves a method of inserting a tool into a disc space between two adjacent vertebrae of a subject, comprising the steps of:
(i) generating three-dimensional preoperative data including information regarding the spatial location of bone structures and nerve positions associated with the two adjacent vertebrae,
(ii) using the three-dimensional preoperative data to plan an oblique posterior entry path, from a pedicle region in an inferior one of the two adjacent vertebrae into the body of the adjacent superior vertebra towards its anterior cortical rim,
(iii) mounting a surgical robot having a control system such that it can define the planned entry path,
(iv) registering the coordinate system of the robot to the three-dimensional preoperative data,
(v) using the controller to ensure that the planned entry path in the coordinate system of the surgical robot, does not approach a nerve position of the subject, as determined in the preoperative data,
(vi) using the surgical robot to generate a drilled hole along the planned entry path, and
(vii) inserting the tool obliquely into the disc space between the inferior and superior vertebrae through the drilled hole.

Yet a further implementation may be for a method of performing spinal stabilization between two adjacent vertebrae of a subject, the method comprising:
(i) drilling two oblique posterior entry passages, one from each pedicle region in an inferior one of the two adjacent vertebrae into the body of the adjacent superior vertebra towards its anterior cortical rim,
(ii) cleaning the disc space between the two adjacent vertebrae,
(iii) inserting an inflatable distraction balloon through a first one of the oblique posterior entry passages into the disc space between the two adjacent vertebrae, and inflating the distraction balloon,
(iv) inserting a screw obliquely into the inferior and superior vertebrae along the other one of the oblique posterior entry passages, such that the vertebrae are mutually fixed in position,
(v) deflating and withdrawing the distraction balloon, and
(vi) inserting a second screw obliquely between the inferior and superior vertebrae along the first one of the oblique posterior entry passages, such that the vertebrae are firmly fixed in position.

This latter method for performing spinal stabilization may further comprise the step of inserting bone grafting material into the disc space, through the first oblique posterior entry passage, after deflation and withdrawal of the distraction balloon. Additionally, in such methods, the oblique posterior entry passages may advantageously be drilled with the aid of a robot. Alternatively, they may be drilled using a mechanical positioner aligned by a surgeon.

A further example implementation may involve a tool for cleaning an intervertebral space, the tool comprising:
(i) a hollow tubular sleeve,
(ii) a central element disposed coaxially within the hollow tubular sleeve, the central element being rotatable relative to the hollow tubular sleeve, and
(iii) at least one flexible cutting element attached to a distal end of the central element, such that rotation of the central element causes the flexible cutting element to morcelize nucleus material in the intervertebral space.

In such a tool, the central element may comprise a screw element, such that the morcelized nucleus material can be removed from the intervertebral space by rotation of the central element. In either of these tools, the flexible cutting element may comprise at least one wire element, which could advantageously comprise at least one loop of wire. In any of these tools, the flexible cutting element may be constructed of a shape memory alloy.

Another exemplary tool described in this disclosure, for cleaning an intervertebral space, may comprise:
(i) a hollow tubular sleeve,
(ii) a central element disposed coaxially within the hollow tubular sleeve, the central element being longitudinally moveable relative to the hollow tubular sleeve, and
(iii) at least one flexible cutting element attached to a distal end of the central element, such that longitudinal motion of the central element of the central element causes the flexible cutting element to operate at different distances from the distal end of the tool,
(iv) wherein the hollow tubular sleeve and the central element are rotatable, such that that rotation of the central element causes the flexible cutting element to morcelize nucleus material in the intervertebral space.

In such a tool, the at least one flexible cutting element may be at least one loop of wire, one of whose ends is attached to the hollow tubular sleeve, and the other of whose ends is attached to the central element, such that longitudinal motion of the central element causes the at least one loop to expand or to contract. The tool may further comprise a screw element, such that the morcelized nucleus material can be removed from the intervertebral space by rotation of the central element. Furthermore, the flexible cutting element may be constructed of a shape memory alloy.

An additional feature in any of the tools mentioned above is that the flexibility of the cutting element may be such that the cutting element changes its angle of attack relative to the axis of the tool as the tool is rotated. The at least one flexible cutting element of the tool may also be operative to clean the end plates of the vertebrae associated with the intervertebral space.

BRIEF DESCRIPTION OF THE DRAWINGS

The presently claimed invention will be understood and appreciated more fully from the following detailed description, taken in conjunction with the drawings in which:

FIGS. 8A to 8C illustrate various implementations of the flexible wire cutting tools used for disc cleaning according to further implementations shown in this disclosure;

DETAILED DESCRIPTION

The current disclosure describes exemplary robotic devices and a robotic procedure for performing minimally invasive spinal stabilization, using only two screws inserted in an oblique trajectory from an inferior vertebra pedicle into the adjacent superior vertebra body. The procedure can be less traumatic than the previously described procedures using oblique trajectories, by executing the trajectory drilling in a minimally invasive manner through two stab incisions, using a robotic arm such as the SpineAssist supplied by Mazor Surgical Technologies Ltd. of Caesarea, Israel, to guide the surgeon along a safe trajectory. The robot arm is essential in such a minimally invasive procedure since no access is provided for direct viewing of the anatomical landmarks, and the high accuracy required for oblique entry can only be generally achieved using robotic control.

Figure 1A:
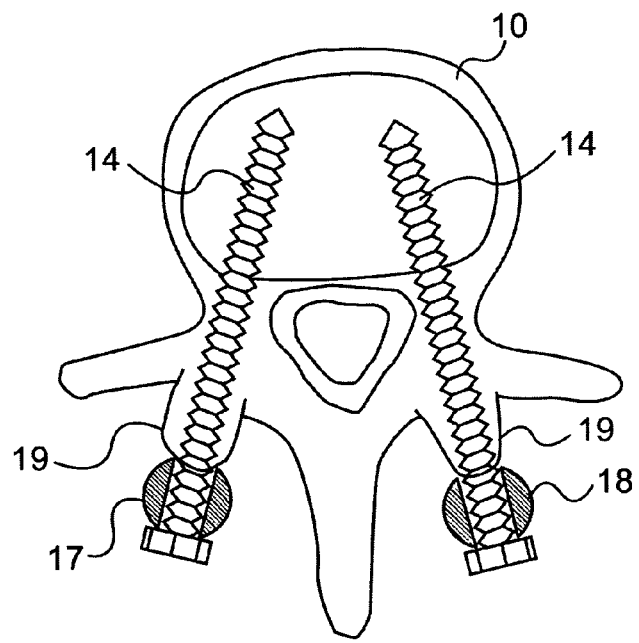
FIGS. 1A-1B show a prior art fusion of two vertebrae by insertion of a pair of screws into each of the vertebrae, and connection of the screw heads by two rigid rods.
Figure 1B:
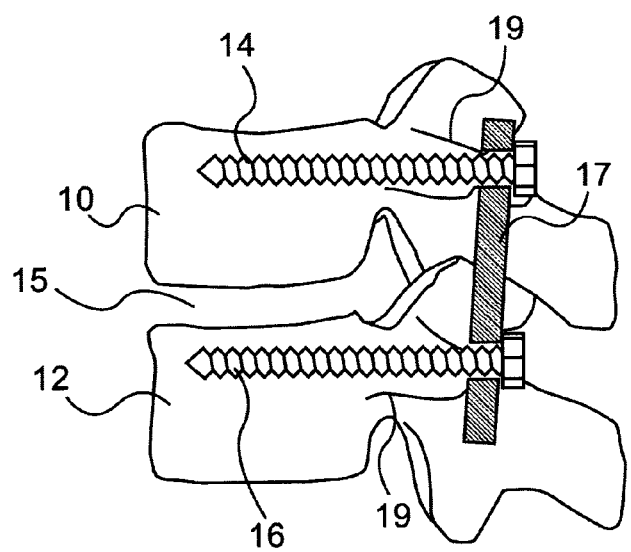
Figure 2A:
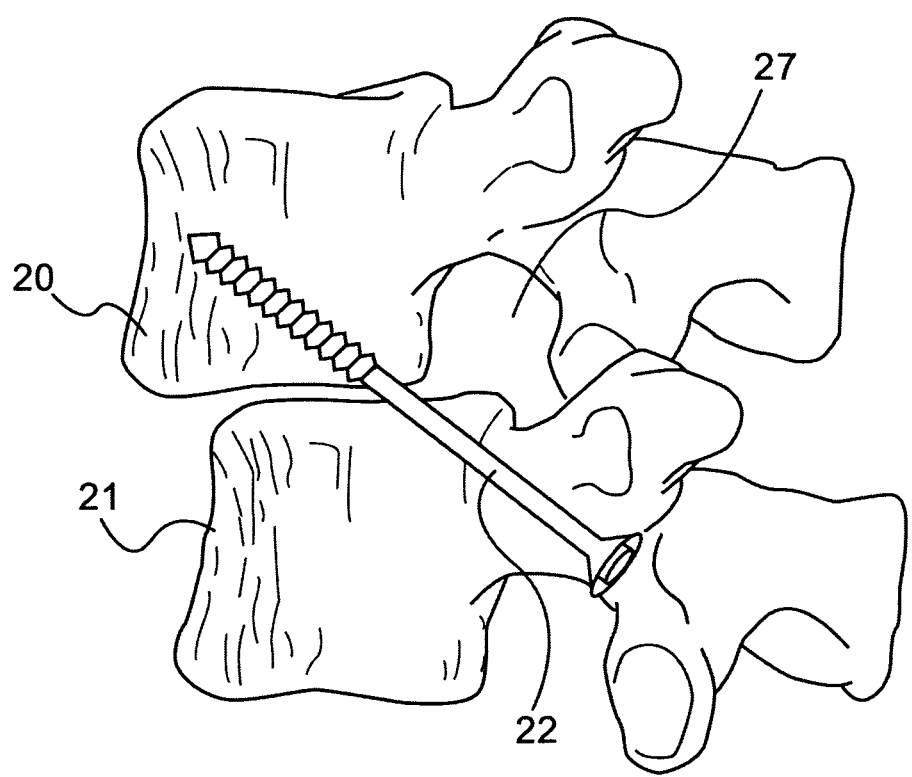
FIGS. 2A-2C illustrate schematically various views of the fusion of two vertebrae by insertion of a pair of screws between the two vertebrae.
Figure 2B:
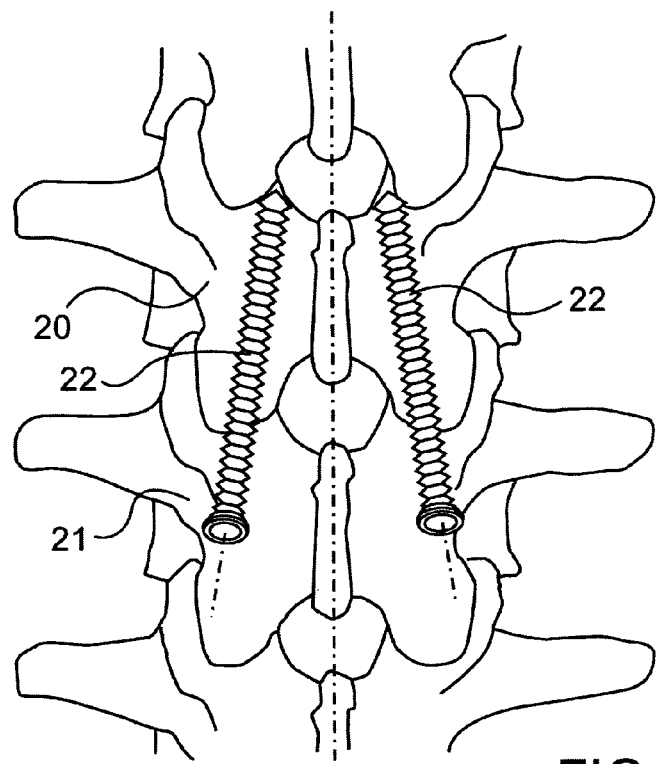
Figure 2C:
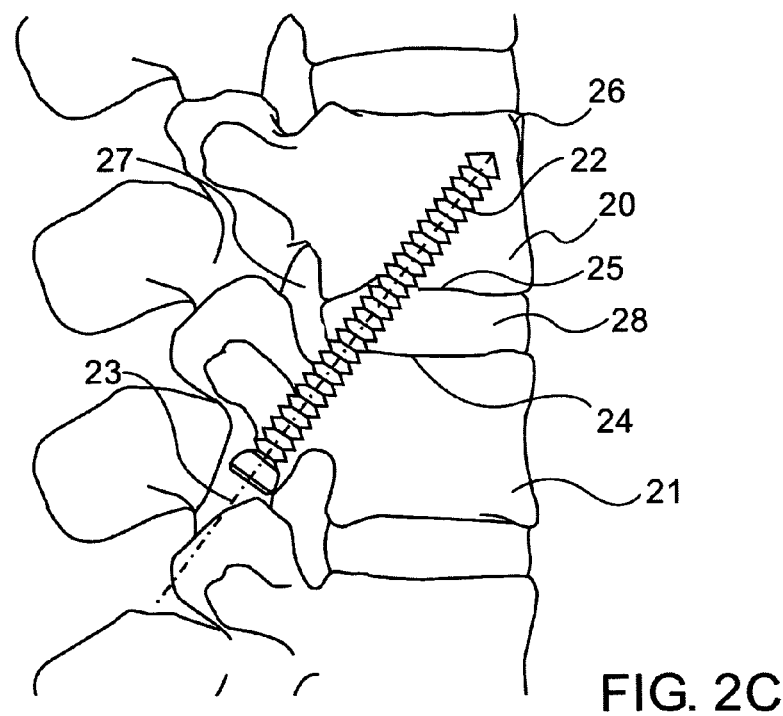
Figure 3A:
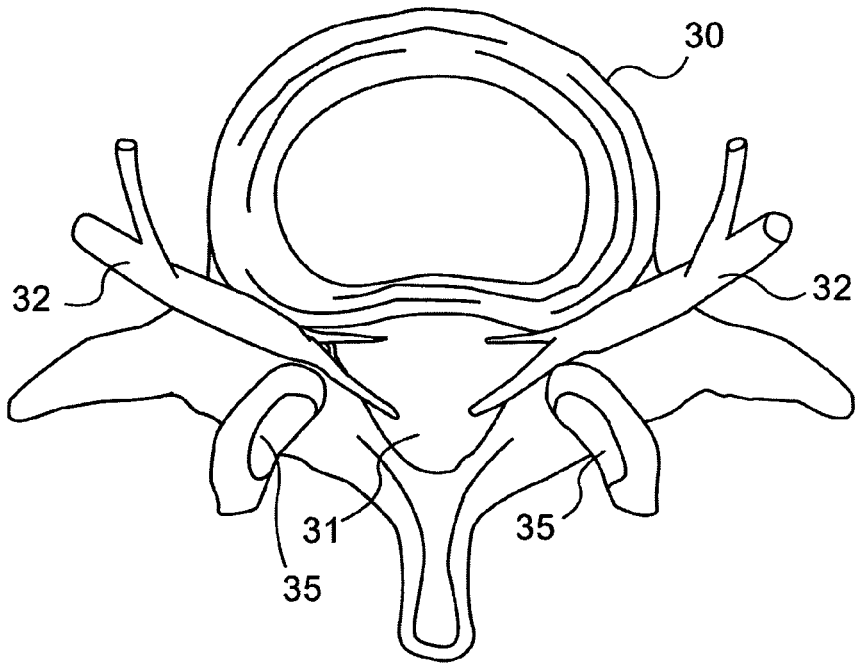
FIGS. 3A and 3B are schematic illustrations of sections of the spine showing how the nerve roots emerge laterally from the spinal column through the foramina.
Figure 3B:
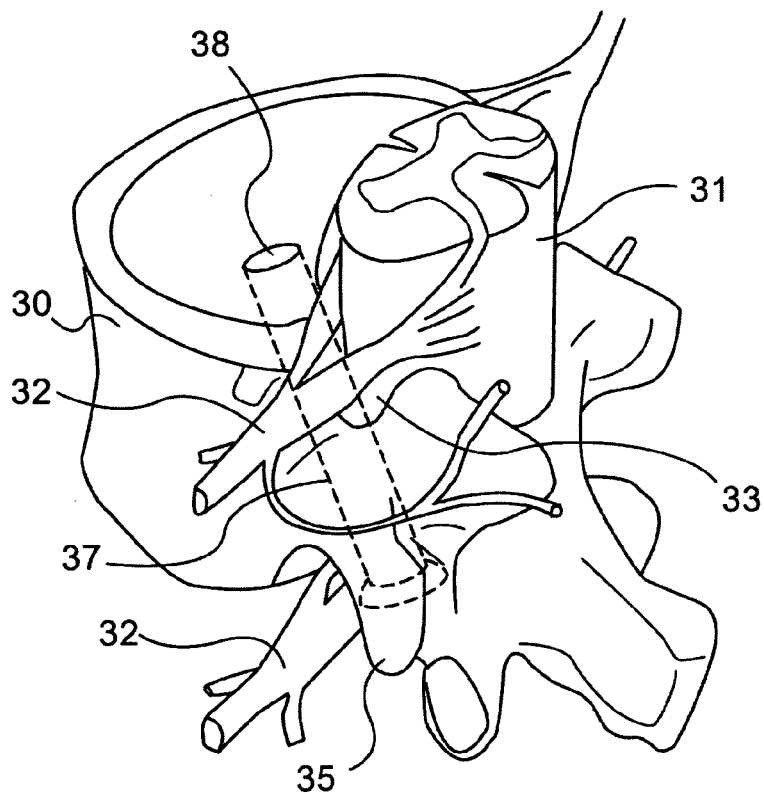

Reference is now made to FIGS. 3A and 3B which are illustrations of sections of the spine showing how the nerve roots emerge laterally from the spinal column through the foramina, from a position just next to or superior the facet joint, and descend downwards laterally of the pedicle. FIG. 3A is a cross sectional view of a vertebra 30, showing the spinal cord 31 and its nerve roots 32 exiting the spinal channel at the intervertebral foramen 33 and extending laterally outwards just anterior to the facet joint 35. FIG. 3B is an isometric view of a single vertebra 30, showing how the nerve root 32 bends downwards after leaving the foramen 33 of the spinal bone structure. As a consequence of this three-dimensional topography of the nerves, the path of a screw trajectory 37, as shown in the dotted outline in the vertebra of FIG. 3B, running from the pedicle of an inferior vertebra, diagonally upwards across the disk space 38 towards the anterior cortical rim of a superior vertebral body passes very close to and just below the nerve 32 where it exits the foramen 33. Therefore unless the screw trajectory is drilled with very high accuracy, there is danger of damage to a nerve root or spinal cord. Furthermore, in order to reach the superior vertebra, the angle being drilled in the pedicle does not coincide with the axis of the pedicle. There is therefore a danger that if an accurate trajectory is not used, the drill may break out of the cortical wall of the pedicle, causing collateral damage.

The possibility of nerve damage may be the main reason why the prior work of Grob and colleagues was performed using a surgical approach involving a standard posterior exposure of the involved vertebrae, such that the surgeon could see the exact path being drilled, and align it to avoid the nerve roots.

In the preoperative planning stage of the present method, the surgeon plans the screw locations and entry trajectories generally on a set of CT scans, where 3D views of the operating site are available. Although CT scans are currently the most generally used three-dimensional imaging techniques, it is to be understood that other imaging techniques, such as MRI or Ultrasound may equally well be used. CT scan data will be used in this application as an illustrative and non-limiting three-dimensional imaging method. The surgeon uses specific criteria which enable him to choose the safest path with the least danger to nerve roots in the vicinity of the operation site. The position of the nerve roots can be marked on the CT scan data, such that these positions can be avoided when the insertion trajectory is planned. Since a conventional spinal CT scan does not show nerve tissue, when using CT data, the surgeon can estimate nerve positions based on the features of the spinal bone anatomy, and the surgeon's knowledge of where the nerves are disposed relative to those features. Since the nerves are directly visible in MRI imaging, if such an imaging modality is used, the nerve positions can be used directly by the surgeon in his preoperative plan.

The preoperative CT scans are then registered to the intraoperative imaging system, commonly a fluoroscope imaging system. One method of performing such image registration is by use of an image processing system to compare certain of the subject's anatomical topological features in the CT scans with those same features in the fluoroscope images. Additionally, the co-ordinate system of the robot must be registered to the fluoroscope co-ordinate system so that the robot pose can be related to the fluoroscope images. This can typically be done by use of a three dimensional marker target, whose position and alignment is known relative to that of the robot, such as by mounting it on the same baseplate as is used by the robot, and whose image is then defined in the fluoroscope system, thus registering the robot's absolute frame of reference with the image co-ordinate system of the fluoroscope. As an alternative to the use of a target, a navigational system can be used, detecting the robot position and the position of a vertebra by means of markers, such as LED's or retroreflectors attached to each, whose positions are correlated using the navigation system. Alternatively, the positions of known anatomical landmarks and known points on the robot can be related by use of a monitored touch tool. Once this registration procedure is complete, the robot can then be programmed to guide the surgical tool along the safe trajectory as planned by the surgeon.

Figure 4A:
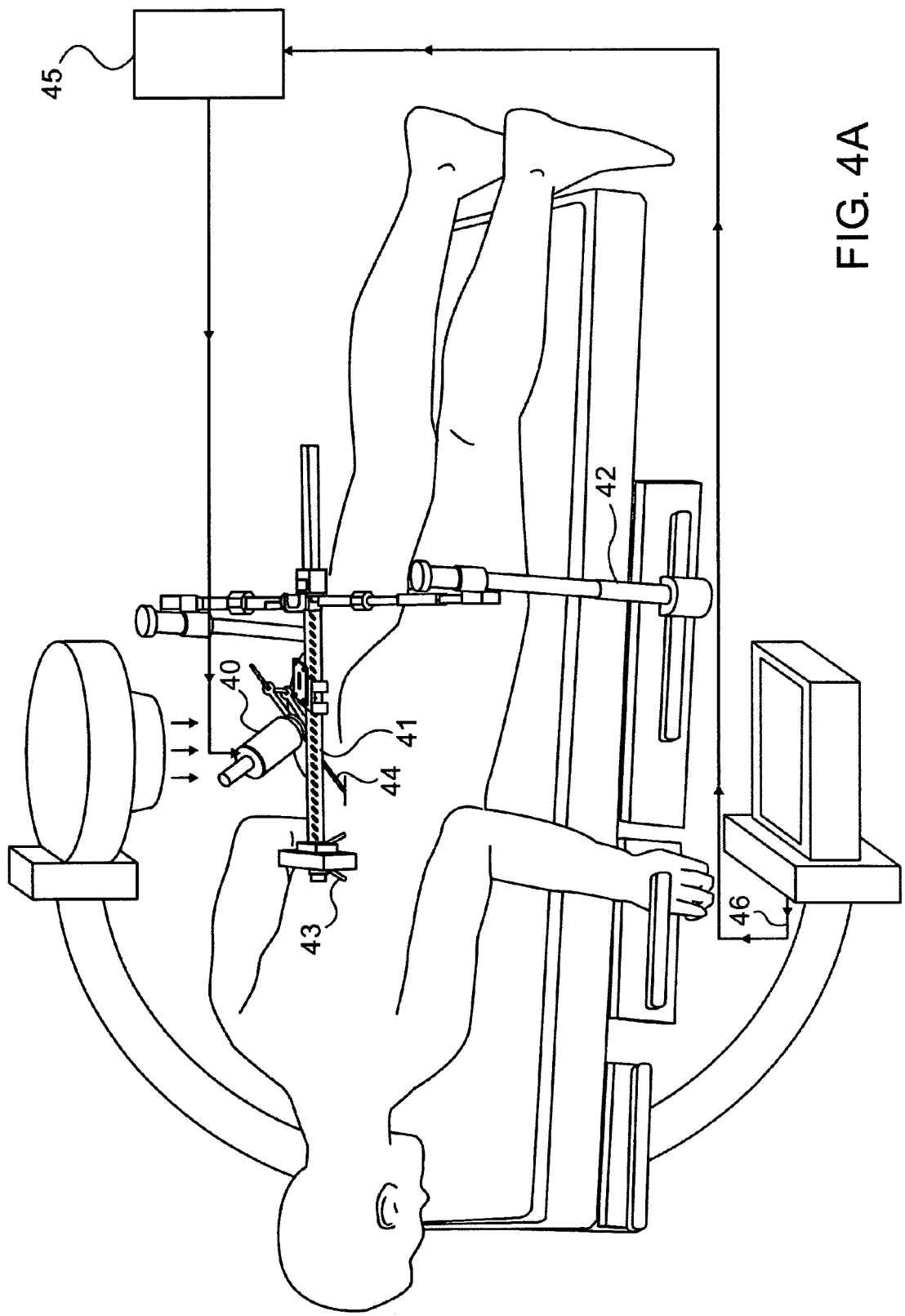
FIG. 4A is a schematic drawing of a robotic system of the present disclosure, mounted on a patient's back, ready for performing oblique screw trajectory drilling.
Figure 4B:
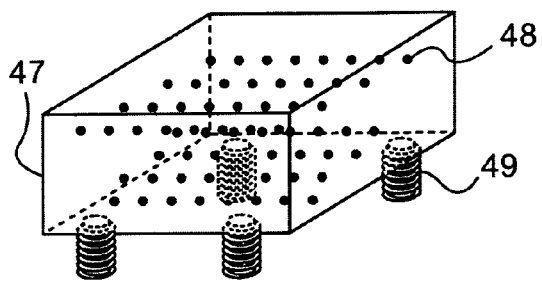
FIG. 4B is a typical three dimensional target, such as is used for the robot co-ordinate registration process.

Reference is now made to FIG. 4A, which is a schematic drawing of the robotic system mounted on a patient's back, ready for performing the oblique screw trajectory drilling method described in this disclosure. The robot 40 is mounted on a bridge assembly 41 supported by clamping or by use of one or more K-wires 43 to vertebrae of the spine and/or the pelvis, and also optionally clamped to the operating table 42. Use of this additional clamping to the operating table increases the stability of the robot under conditions when force may be applied to the robot during the drilling process, which may cause it to move as the drilling process exerts forces on the spine. In addition, a rigid reference by clamp or K-wire 43 is made to the spine, so that the robot's position is fixed relative to the bones being operated on by the robot. The robot is not generally used to perform the drilling itself, but rather to align a tool guide 44 in the calculated position and direction, such that the surgeon can then perform the procedure using that tool guide to ensure an accurate and safe entry path. However, it is to be understood that the use of the robot is not intended to be limited to aligning a tool guide, and that the application is intended to also cover more active use of the robot in performing the procedure, such as in drilling the hole itself. The control system 45 is adapted to utilize input data from CT scans stored preoperatively to implant the surgeon's selected entry path onto that data. The CT scans should include data on the vertebral anatomy and the control software should be capable of using the position of the nerves determined from this vertebral anatomy, as forbidden areas for the insertion trajectory to pass through or to pass nearby. The system thus provides assistance to the surgeon by showing him potential collision paths of his/her planned insertion trajectory with nerves lying in its path. According to an alternative implementation of the control system, such a routine could ensure that even if the surgeon inadvertently plans a hazardous insertion trajectory path, the control system would not enable the surgeon to execute such a plan, by blocking that robot pose. Additionally, in some oblique entry procedures, especially those performed in the sacral region on patients suffering from lordosis, the angle of insertion may be close to axial alignment with the spine, such that the drill trajectory may collide with the pelvic bone. Thus, collisions with bone structures may also be taken into consideration in programming blocked poses of the robot. When MRI is used as the imaging modality, nerves are also seen, and their imaged position may be used directly for planning the insertion trajectory. The registration between the preoperative CT data and the true life world of the robot co-ordinate system, as determined, for instance, on real time C-arm fluoroscope images 46, can be performed by any of the known registration methods, such as those mentioned above. One exemplary implementation of a three dimensional target 47, such as can be used for registering the robot co-ordinate system to that of the fluoroscope system is shown in Fig, 4B. This target 47 is a three dimensional body, transparent to X-rays, containing preferably two layers of radio-opaque marker balls 48, whose positions are known, such that analysis of the positions of the marker balls on an X-ray image of the target can be used to determine the three dimensional orientation of the target. The exemplary target shown has a set of screws or pins 49, for attaching it to the same base as that used by the robot, such that it has a known geometric relation to that of the mounted robot, and once its position and orientation is known from analysis of images, so is the position and orientation of the robot known.

Although the system and method has been described hereinabove for use in spinal fusion, it is also possible to use the same oblique entry procedures and system for dynamic stabilization of the spine without fusion. This can be achieved by having a flexible rather than a rigid connection between the vertebrae. The oblique fixing screws are then provided with a somewhat flexible region along part of its length to enable limited motion between the two vertebrae. Such an application has been described in US Patent Publication No. US 2009/0112269 to I. H. Lieberman et al., one of the inventors of the present application, and assigned to The Cleveland Clinic Foundation.

In order to obtain good bone fusion, it is necessary to clean the disc space to remove the disc nucleus and to insert bone graft or any kind of bone substitute that will encourage interbody bone growth and bony fusion. By following these procedures bone can grow well, and achieve a bony fusion. Furthermore, it is possible to use the oblique entry screws to fix adjacent vertebrae in combination with some posteroior fusion techniques, such as postero-lateral/medial fusion across the facet joints or between transverse processes, instead of inter-body fusion. In such a procedure, no cleaning and bone graft of the intervertebral space is needed. Also in the case of dynamic stabilization of the spine without fusion, no disc cleaning and bone graft is needed.

In addition to the drilling and screw insertion, more steps are required to complete the procedure. These steps include: nucleus morcelizing, nucleus remnant removal/evacuation, vertebrae end-plate scraping and in some cases vertebrae distraction.

There exist commercial tools for disc morcelizing and removal of the nuclear material. In most cases, these prior art tools are inserted from the subject's lateral side, radially to the disc space. This involves the drilling of additional holes in the annulus, even for minimally invasive methods, besides the hole or holes required for the insertion of the fixation screws. Since the annulus has important support characteristics for the disc, such additional holes in the annulus may considerably affect the strength of the intervertebral support. The oblique approach, on the other hand, obviates the need for such additional holes, by accessing the nucleus of the disc other than through the annulus itself. Furthermore, since the oblique posterior entry methods described in this disclosure provide access to the disc space, which non-oblique entry methods can only access by lateral entry, this method enables the disc morcelizing and removal tools to be inserted without the need to make any additional holes at all, besides the oblique ones drilled for the fixation screws themselves.

Disc cleaning and removal through the oblique trajectory requires understanding of the three dimensional structure in a more detailed way. This is illustrated by reference to FIGS. 5 and 6.

Figure 5:
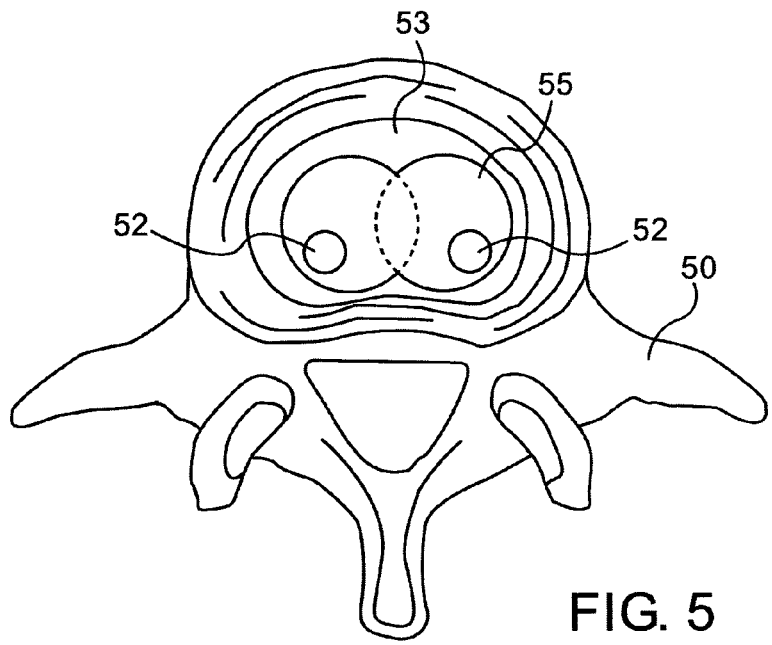
FIGS. 5 and 6 are schematic views of the spine, showing how the disc cleaning and removal procedures through the oblique trajectory holes, as described in this disclosure, relate to the structure of the vertebrae.

Reference is first made to FIG. 5, which is a schematic cross-sectional view of the disc region of a vertebra 50 showing the two holes 52 through which the drilling path of the oblique trajectory enters the disc nucleus space 53. The drilled hole typically has a diameter of about 4 to 5 mm. A disc cleaning tool of the type described hereinbelow, having a flexible wire head, is inserted through one of the drilled working channels into the nucleus space, and rotation of the tool enables the wire head to detach and morcelize the nucleus tissue in the region 55 surrounding the hole exit. These tools differ from prior art tools in that the cutting blades are constructed of flexible wires, so that the angle of attack relative to the tool axis can vary as the tool is rotated. Use of a flexible wire head enables the tool to cover the space within the disc annulus, in spite of the axis of rotation of the tool being at an angle to the axis of the disc space. Once the area within the range of the cleaning head has been morcelized, the tool is withdrawn and inserted through the other hole, and the procedure repeated therein. Since the two treated regions overlap, selection of suitable placement of the holes enables the entire disc region to be cleaned of the tissue of the disc by this means.

Figure 6:
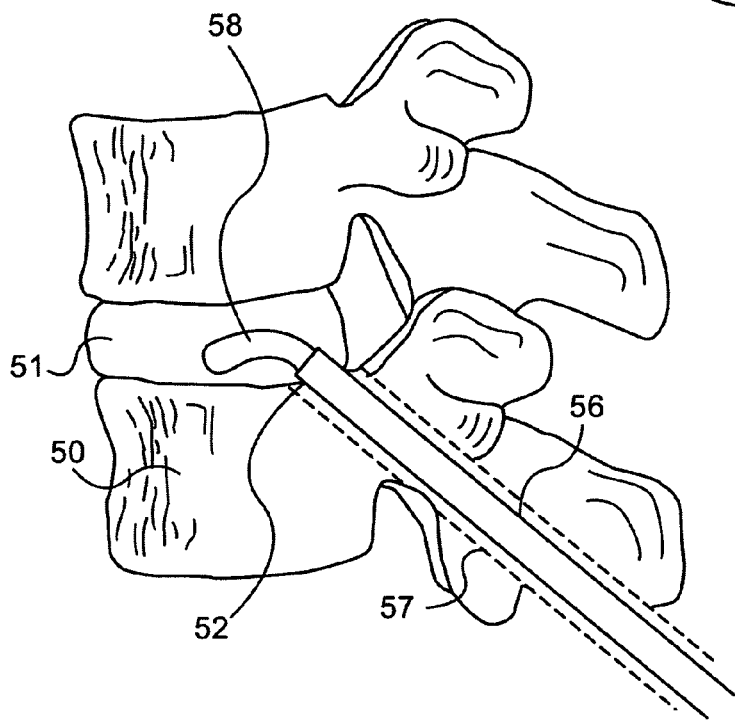

FIG. 6 is a lateral view of the treated vertebral region, showing the cleaning tool 56 passing through one of the oblique trajectory holes 57 in order to access the disc region 51 for cleaning. As the tool is rotated, the end cutter wires 58 flex with the rotation and thus are able to cut and morcelize the tissue over a wider area of the disc than would be possible with a rigid headed tool operated in the same location. Since the wire cutting head 58 can be extended or retracted from the tool sleeve 56, it can be adjusted to cover essentially the whole of the internal volume of the disc situated on its side of the disc.

Figure 7:
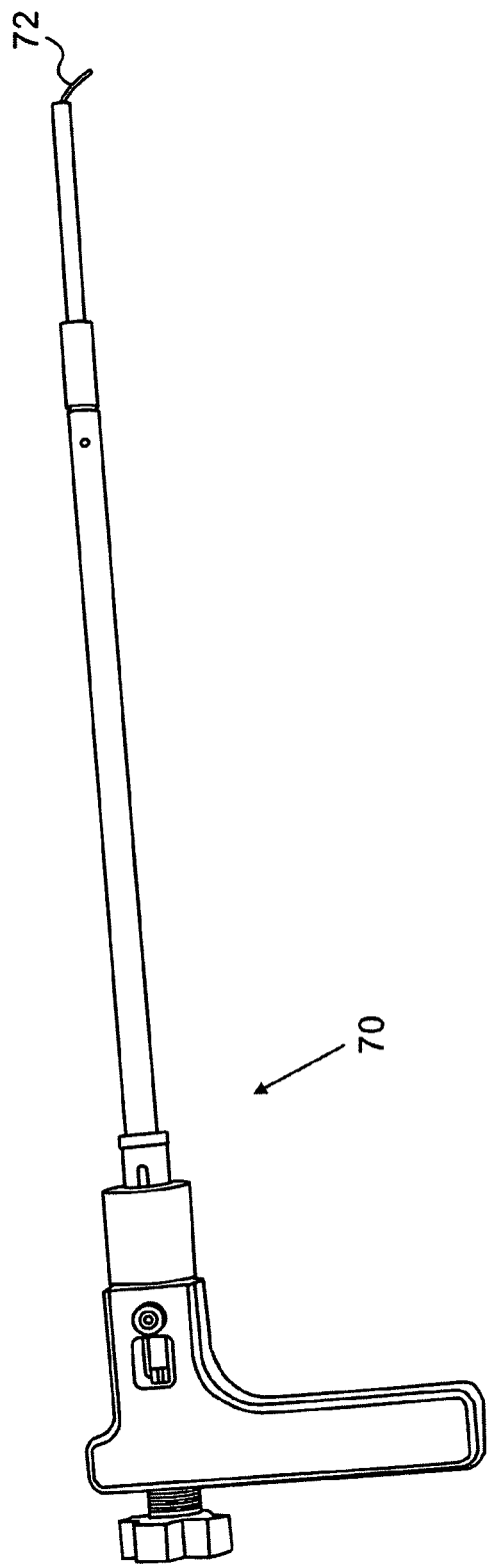
FIG. 7 is an illustration of a nucleus morcelizing tool, adapted to use a flexible wire cutter at its distal working end.

FIG. 7 is an illustration of a commercially available nucleus morcelizing tool 70, adapted to use a flexible wire cutter 72 at its distal working end.

Figure 8A:
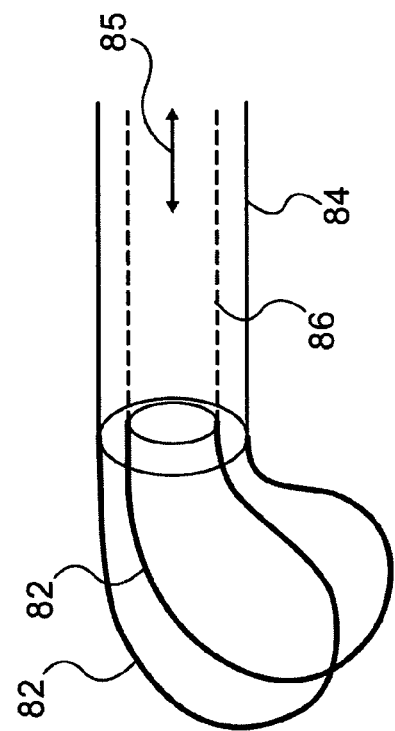

Reference is now made to FIGS. 8A to 8C which illustrate various typical implementations of the flexible wire cutting tools used for disc cleaning according to a further implementation of the present invention The disc cleaning tool, shown in FIG. 8A, is composed of two modular parts:
1. The cutting head, which is made of a pair of loops of spring material 82.
2. The handle 84, which comprises an outer tube or sleeve with an inner coaxial element 86, which can be a rod or a tube, the inner element being capable of longitudinal movement 85 relative to the outer tube.

One end of each of the two loops of spring material 82 is attached to the inner element 86, while the other end of each of the two loops of spring material is attached to the outer tube 84. As the inner element is pushed distally, the length of the two loops increases, such that they can access and clean points within the vertebral disc space further from the end of the tool handle. As the inner element is retracted, the loops can access the disk space closer to the end of the tool handle.

Figure 9:
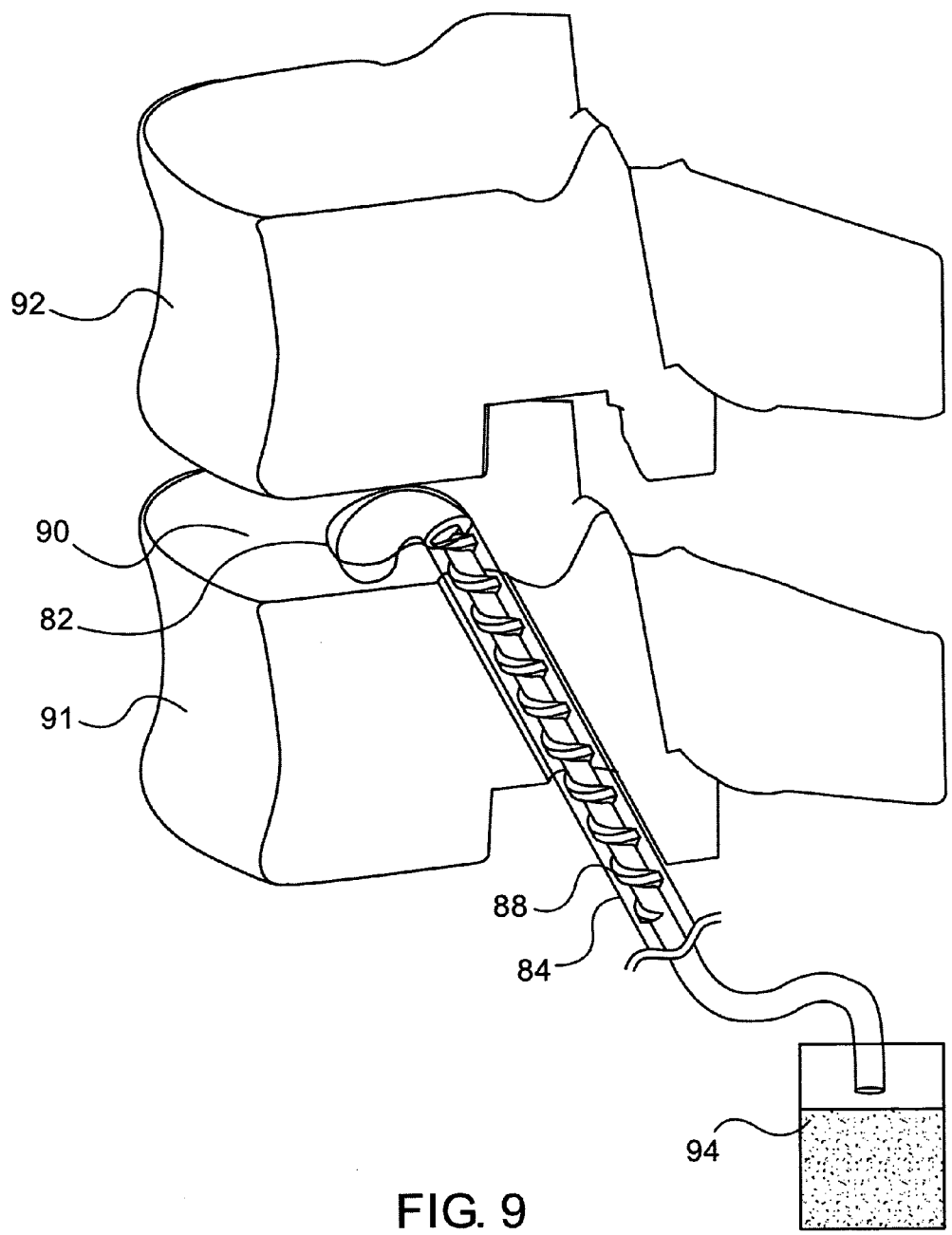
FIG. 9 is a schematic illustration of a complete disc evacuation system implementing a screw pump tool, as shown in FIGS. 8B and 8C above.

Furthermore, retraction of the inner element enables the surgeon to move nucleus material detached from points further from the tube end towards the tube end, from where it can be disposed of, down the tube. The inner element 86 is generally constructed in the form of a tube such that the dislodged nuclear material can be removed through the tube, as shown in FIG. 9 below.

Since the extent of the region in which the tool performs its cutting action can be readily controlled using the position of the inner element, this tool enables the user to operate it in a safe and simple way without any need for additional observation systems, such as a laparoscopic vision system.

FIG. 8B is a schematic rendering of another tool for use in cleaning the inner volume of a vertebral disc. This tool has a pair of loops of wire as its cutting head arranged in the form of a propeller 87. In addition, an Archimedes screw 88 is shown in the barrel of the tube 84, such that nucleus material detached from within the disc can be transported out of the disc for disposal as the tool head is rotated. FIG. 8C illustrates an alternative cutting head, using a pair of flexible wires arranged like a double tailed whip 89.

The cutting blades of all of the tools for use in the disc cleaning operations using the current oblique entry technique can advantageously be made of a shape memory material, such as Nitinol, so that they can be inserted at the end of the tool through the oblique bore in a folded position, and will deploy to their operating configuration on exit from the bore into the disc space. Furthermore, these tools differ from prior art tools in that the cutting blades are constructed of flexible wires, so that the angle of attack relative to the tool axis can vary as the tool is rotated, to enable the cutting head to achieve a larger reach within the disc annulus than would be possible with a rigid cutting head. Additionally, such tools with flexible wire cutting heads, are able to clean the end plates of both the superior and the inferior vertebrae simultaneously and essentially equally well, even though the access to the superior vertebra end plate is substantially better than to the inferior vertebra end plate, because the angle at which the cleaning tool faces the superior vertebra end plate is more "face-on" than the inferior vertebra end plate. With a radially inserted tool, this problem does not arise since both end plates face the tool at equal alignments.

Devices exist for disc cleaning, generally entering the disc space radially, though Trans1 Inc, have described an axial approach in their AxiaLIF® procedure, though this is limited to the sacral region, for L5-S1 treatment. The AxiaLIF® procedures and the tools used are described in U.S. Pat. No. 6,558,390 and subsequent patents and applications assigned to Trans1. The tools used for morcelizing the disc nucleus material, unlike the tools of the present disclosure, generally have a rigid cutting head, as they operate in an almost axial position, and therefore do not have or need the flexibility to change operating angle with rotation of the tool. However, as previously stated, none of the previously described methods is designed to enter the disc space in a truly oblique manner.

References now made to FIG. 9, which is a schematic illustration of a complete disc evacuation system implementing a screw pump tool, as shown in FIGS. 8B and 8C above. The tool is shown operating within a disc space 90 between an inferior 91 and superior 92 vertebra. It is power operated, typically being rotated at speeds of between one and a few revolutions per second and can use the generic hospital suction system to pump out the morcelized material removed from the disk space into a waste container 94. This system can be operated through the oblique trajectory.

Figure 10:
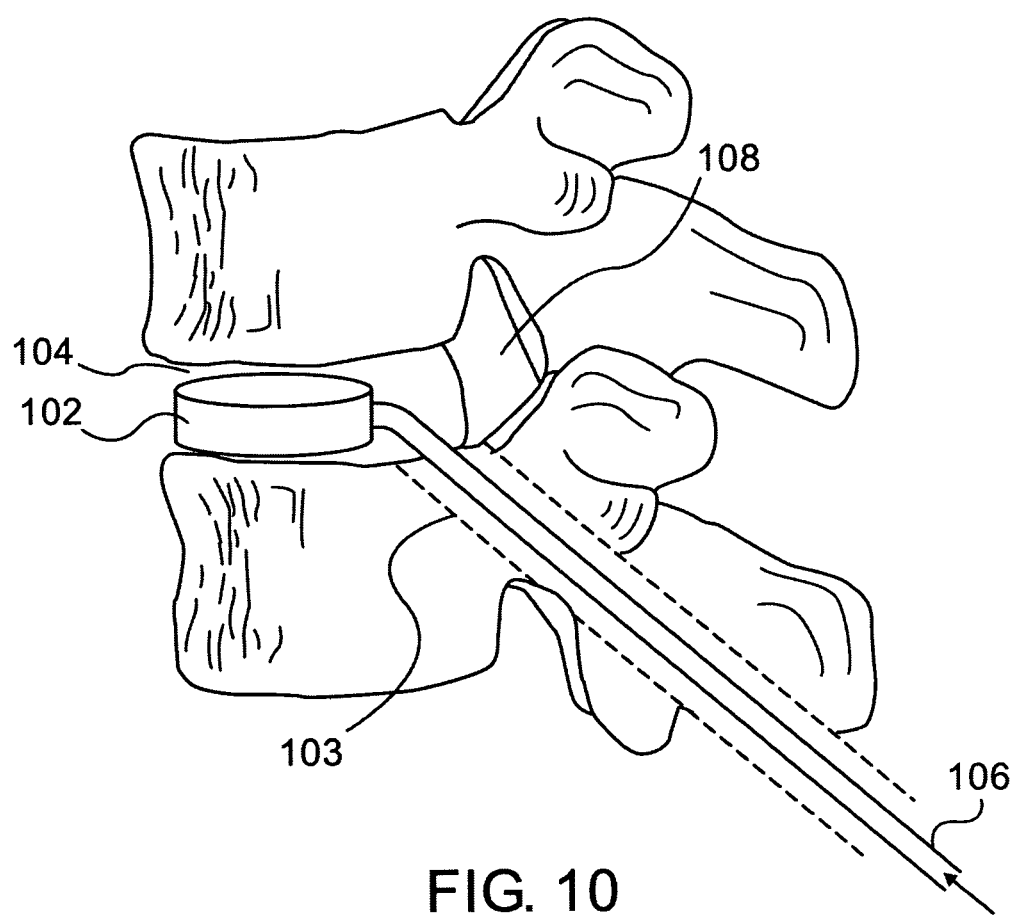
FIG. 10 shows a vertebral distraction device composed of an inflatable balloon inserted through one of the obliquely drilled holes.

Reference is now made in FIG. 10 which shows a vertebra distraction device composed of an inflatable balloon 102 inserted through one of the drilled holes 103 from the pedicle region into the vertebral disc space 104, and then inflated by means of an inflation tube 106 to generate opposing forces on the two neighboring vertebrae, thus enabling decompression and release stenosis. Once distraction is achieved, one of the oblique screws is inserted to affix the vertebrae at the distracted position. The balloon is then deflated and taken out of the disc space, with the disc positions maintained by the first inserted oblique screw. Bone graft is then inserted through the second drilled hole from which the deflated balloon was withdrawn, following which, the second oblique screw is inserted to complete the fixation of the two vertebrae.

FIG. 10 also illustrates well how the oblique hole passes very closely to the intervertebral foramen 108, and the consequent need for high accuracy when drilling such holes to avoid damage to the nerves exiting the spinal column at the foramina. This emphasizes the advantage in the use of robotic control and drilling when generating such oblique holes.

The oblique approach described in this disclosure has an additional advantage over prior art lateral or radial approaches, where additional holes have to be made in the annulus of the disc in order to clean it, to perform distraction, or to insert an interbody support such as a cage. Since the annulus has important support characteristics for the disc, this additional hole in the annulus may considerably affect the strength of the intervertebral support. The oblique approach, on the other hand, obviates the need for such an additional hole, by accessing the nucleus of the disc other than through the annulus itself.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for performing a minimally invasive spinal stabilization procedure between two adjacent vertebrae of a subject, the system comprising:
    a surgical robot mounted such that it defines at least one path for oblique screw insertion from the pedicle region in an inferior one of said two adjacent vertebrae into the body of the adjacent superior vertebra, towards its anterior cortical rim;
    a control system receiving three-dimensional preoperative data, including information regarding the spatial location of the bone structures and the nerve positions of said two adjacent vertebrae; and
    a registration system to relate the coordinate system of said surgical robot with said three-dimensional preoperative data,
wherein said control system is adapted to use said information to determine a safe path for said oblique screw insertion, such that said spinal stabilization procedure can be performed by minimally invasive techniques without direct viewing of anatomical details of said vertebrae.

2. A system according to claim 1, wherein said at least one safe path is a path in the coordinate system of said surgical robot, which does not approach either the course of a nerve of the subject, or a bone structure of the subject which it is not intended to intersect, as determined from said three-dimensional preoperative data.

3. A system according to claim 1, wherein said three-dimensional preoperative data is obtained from any one of CT scans, MRI scans and ultrasound images.

4. A system according to claim 1, wherein said control system is adapted to inhibit said robot from executing a path in the coordinate system of said surgical robot, which would approach the course of a nerve of the subject, as determined in said three-dimensional preoperative data.

5. A system according to claim 1, wherein said safe path passes through a pedicle of said inferior vertebra, and is determined by said control system using criteria which further ensure that said safe path does not break out of the cortical wall of said pedicle.

6. A system according to claim 1, wherein said registration system comprises an image processing module for comparison of anatomical topological features of the subject in said three-dimensional preoperative data with those same features in fluoroscope images of said vertebrae.

7. A system according to claim 1, wherein said registration system includes a target having predefined marker features, said target being disposed in a predetermined position and orientation relative to said robot, such that images of said target in said fluoroscope images enable the co-ordinate system of said robot to be related to that of fluoroscope images of said vertebrae.

8. A system according to claim 1, wherein said registration system utilizes a navigational system to relate the co-ordinate system of said robot to fluoroscope images of said vertebrae.

9. A method for performing a minimally invasive procedure for spinal stabilization between two adjacent vertebrae of a subject, the method comprising:
    generating three-dimensional preoperative data including information regarding the spatial location of the bone structures and nerve positions associated with said two adjacent vertebrae;
    using said three-dimensional preoperative data to plan at least one safe path for oblique screw insertion, from the pedicle region in an inferior one of said two adjacent vertebrae into the body of the adjacent superior vertebra towards its anterior cortical rim;
    mounting a surgical robot such that it can delineate said at least one safe path;
    registering the coordinate system of said robot to said three-dimensional preoperative data;
    utilizing said surgical robot to generate a drilled hole along one of said at least one planned paths; and
    inserting a screw obliquely between said inferior and superior vertebrae through said drilled hole.
    wherein said method enables said spinal stabilization procedure to be performed by minimally invasive techniques without direct viewing of anatomical details of said vertebrae.

10. A method according to claim 9, wherein said at least one safe path is two safe paths, one on each lateral side of said vertebrae, such that two screws may be inserted obliquely between said inferior and superior vertebrae.

11. A method according to claim 9, wherein said at least one safe path is planned to avoid undesired collisions with a bone structure of the subject, or encroachment on the path of a nerve of the subject.

12. A method according to claim 9, wherein said step of registering the coordinate system of said robot to said three-dimensional preoperative data comprises the step of comparing anatomical topological features of the subject in said three-dimensional preoperative data with those same features in fluoroscope images of said vertebrae.

13. A method according to claim 9, further comprising the step of disposing a target having predefined marker features in a predetermined position and orientation relative to said robot, such that images thereof in said fluoroscope images enable the co-ordinate system of said robot to be related to that of fluoroscope images of said vertebrae.

14. A method according to claim 9, further comprising the step of relating the co-ordinate system of said robot to fluoroscope images of said vertebrae by means of a navigational system.

15. A system according to claim 1, wherein said system enables performance of said minimally invasive spinal stabilization procedure on non-spondylolisthesic subjects.

16. A method according to claim 9, wherein said method enables performance of said spinal stabilization procedure on non-spondylolisthesic subjects.

17. A method for performing spinal stabilization between two adjacent vertebrae of a subject, the method comprising:
    drilling two oblique posterior entry passages, one from each pedicle region in an inferior one of said two adjacent vertebrae into the body of the adjacent superior vertebra towards its anterior cortical rim;

cleaning the disc space between said two adjacent vertebrae;

accessing said disc space between said two adjacent vertebrae through a first one of said oblique posterior entry passages, and distracting said two adjacent vertebrae;

inserting a screw obliquely into said inferior and superior vertebrae along the other one of said oblique posterior entry passages, such that said vertebrae are mutually fixed in position; and inserting a second screw obliquely between said inferior and superior vertebrae along the first one of said oblique posterior entry passages, such that said vertebrae are firmly fixed in position.

18. The method of claim 17, further comprising the step of inserting bone grafting material into said disc space through said first oblique posterior entry passage after distracting said two adjacent vertebrae.

19. The method of claim 17, wherein said oblique posterior entry passages are drilled with the aid of a robot.

20. The method of claim 17, wherein said oblique posterior entry passages are drilled using a mechanical positioner aligned by a surgeon.

21. The method of claim 17, wherein said method enables performance of said spinal stabilization procedure on non-spondylolisthesic subjects.

* * * * *